United States Patent [19]

Mishell et al.

[11] Patent Number: 4,978,622
[45] Date of Patent: Dec. 18, 1990

[54] CYTOPHAGA-DERIVED IMMUNOPOTENTIATOR

[75] Inventors: Robert Mishell; William Usinger, both of Berkeley, Calif.

[73] Assignee: Regents of the University of California, Berkeley, Calif.

[21] Appl. No.: 403,899

[22] Filed: Sep. 1, 1989

Related U.S. Application Data

[63] Continuation of Ser. No. 877,099, Jun. 23, 1986, abandoned.

[51] Int. Cl.$^5$ ................ C08B 00/00; C08B 37/00; A61K 31/715; A61K 39/00
[52] U.S. Cl. .................... 435/274; 435/267; 435/270; 424/88; 514/54; 536/1.1
[58] Field of Search ............ 435/267, 270, 274; 424/88, 89; 514/54; 536/1.1

[56] References Cited

U.S. PATENT DOCUMENTS 4,242,326 12/1980 Sugawara et al. ............ 435/267
4,755,382 7/1988 Flaherty ........................ 424/88

OTHER PUBLICATIONS

Kennedy, *Bioactive Carbohydrates: In Chemistry, Biochemistry and Biology*, Ellis Horwood Ltd., New York, (1983), pp. 66–67.
Usinger et al., Fed. Proc., 44(3): #1097 (1985).
Usinger et al., Curr. Microbiol., 12(4): 203–208 (1985).
Morrison et al., Immunochemistry, 13: 813 (1976).
Usinger et al., Fed. Proc., 42(3): #1582 (1983).
Jahway et al., J. Immunol., 137(7): 2225–2231 (1986).
"Myxobacterial Development and Cell Interactions", edit. by Eugene Rosenberg, Springer Series in Molecular Biology, Springer-Verlag New York Inc., Chapter 6.
"The Pigments of *Flexibacter elegans*: Novel and Chemosystematically Useful Compounds", by Reichenbach and Kleinig. Arch. Microbiol. 101, 131–144 (1974) by Springer-Verlag 1974.
Shiigi, S. M., et al., Journal of Immunology (1975), 115 (3), 741–744.
Shiigi, S. M., et al., Journal of Immunology (1977), 119 (2), 679–684.
Mishell, R. I., et al., in Chemistry and Biological Activities of Bacterial Surface Amphiphiles, Eds Shockman, G. D., et al., J. Academic Press, New York (1981).

Primary Examiner—Esther L. Kepplinger
Assistant Examiner—Toni R. Scheiner
Attorney, Agent, or Firm—Irell & Manella

[57] ABSTRACT

Substantially pigment-free gliding bacteria adjuvant (GBA) is isolated from medium in which Cytophaga strain GB-2 has been cultured by extraction with acetone to remove pigment, enzymatic digestion and filtration to remove residual protein and nucleic acids, and affinity chromatography to remove residual lipopolysaccharide. This pure form of GBA shows unexpectedly high specific immunopotentiating activity relative to crude GBA.

8 Claims, 3 Drawing Sheets

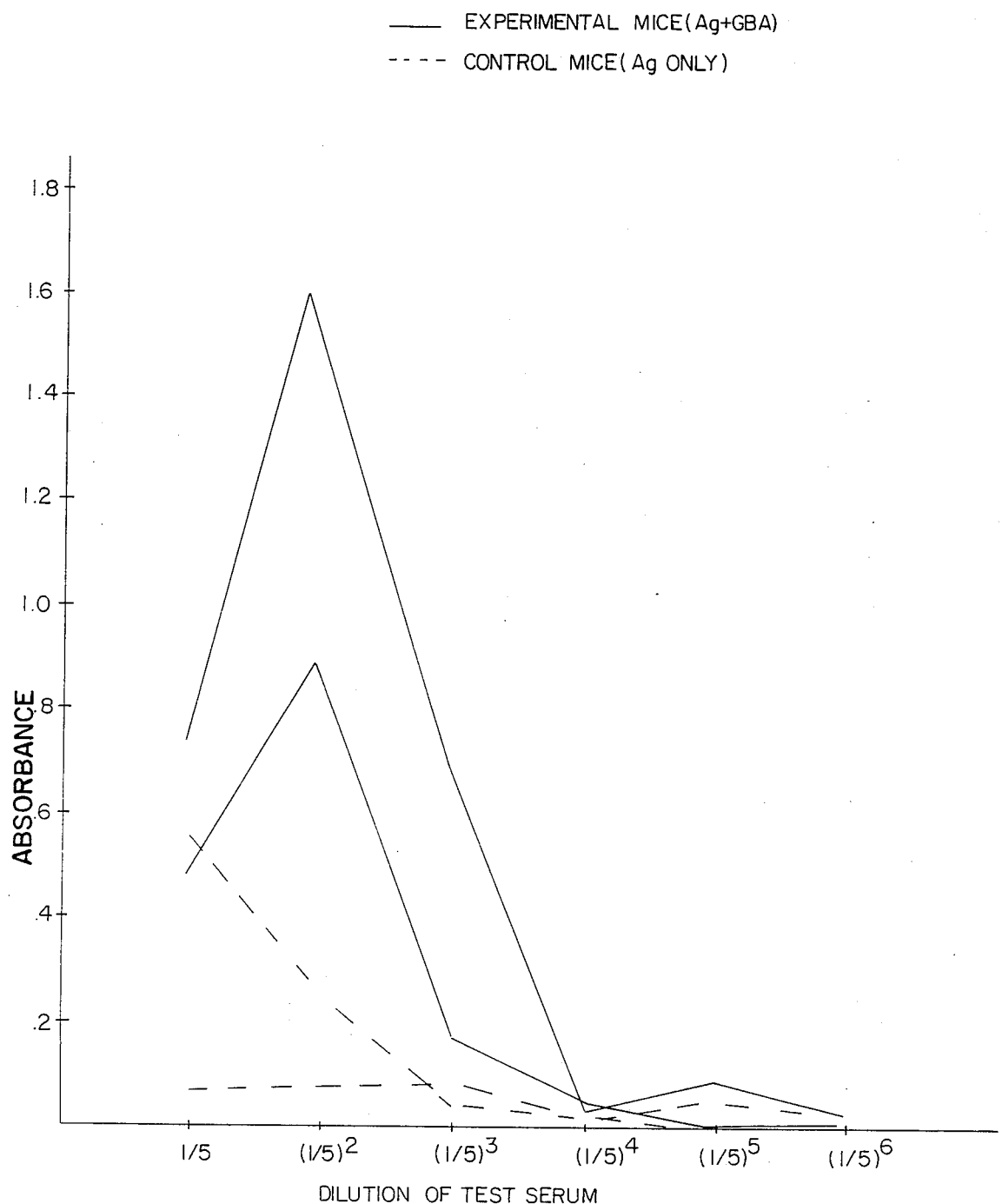

CYTOPHAGA-DERIVED IMMUNOPOTENTIATOR

REFERENCE TO GOVERNMENT GRANT

This invention was made with Government support under Contract N00014-84-K0626 awarded by the Department of the Navy. The Government has certain rights in this invention.

This application is a continuation of application Ser. No. 06/877,099, filed June 23, 1986, now abandoned.

TECHNICAL FIELD

The present invention is the field of immunology in general and immunopotentiators or adjuvants in particular. More specifically, it is directed to a pigment-free exopolymer adjuvant derived from Cytophaga strain GB-2.

BACKGROUND ART

Immunogenicity is the capacity of an antigen to induce a cellular and/or humoral response. Immunopotentiation is the enhancement of such a response or the development of a response to an otherwise nonimmunogenic material. Agents that have the ability to so enhance or develop an immune response are called "adjuvants" or "immunopotentiators". Adjuvants are used to increase the efficacy of vaccines and in the treatment of immunity-associated diseases such as cancer, immunodeficiency, and certain infective diseases.

Many bacterial components have been investigated as immunopotentiators. Among these are components from a psycrophilic gliding bacterium of the genus Cytophaga. This Gram-negative bacterium was originally isolated from a contaminated lot (designated FBS 762) of fetal calf serum (FCS). Shiigi, S. M. and Mishell, R. I., *J. Immunol* (1975) 115:741–745. Medium conditioned by the growth of these gliding bacteria was found to have immunopotentiating activity on cultures of murine splenocytes supplemented with deficient FCS. Studies comparing the adjuvant and mitogenic effects of this medium with those of purified lipopolysaccharide (LPS) from *S. typhosa* indicated the activity of the medium was attributable to substances other than LPS from the gliding bacterium Shiigi, M. S. et al. *J Immunol*, (1977) 119:679–684. A further report regarding this bacterium describes the preparation of exopolymers (EP) from the medium in which the bacterium (then designated *Cytophaga sp*) had been cultured by dialysis and lyophilization. The Ep was characterized as being water soluble and containing ≦0.2% protein and ≦0.001% LPS. It was found to potentiate immune responses to specific antigens and stimulate murine macrophages and macrophage cell lines to release colony stimulating factors and interleukin 1 (IL-1). Mishell, R. I. et al, in *Chemistry and Biological Activities of Bacterial Surface Amphiphiles,* Eds Shockman G. D. and Wicken A. J., Academic press, New York (1981).

DISCLOSURE OF THE INVENTION

The present invention provides a method of obtaining the above described Cytophaga exopolymer from the medium in which the bacterium is cultured in a substantially pigment-free form that exhibits unexpectedly high adjuvant activity. The exopolymer is sometimes referred to herein as "GBA" (gliding bacteria adjuvant) and the Cytophaga species that sheds or secretes it as "GB-2".

Accordingly, one facet of this invention is substantially pigment-free GBA.

Another aspect of the invention is a method of isolating substantially pigment-free GBA from medium in which GB-2 has been cultured comprising precipitating the GBA with acetone whereby pigment is extracted from the GBA. In a preferred embodiment of this method, residual protein and lipopolysaccharide are removed from the pigment-free GBA, respectively, by proteolytic digestion and filtration and by affinity chromatography Yet another aspect of the invention is a method of potentiating an immune response in a subject comprising administering an immunopotentiating amount of substantially pigment-free GBA to the subject.

Still another aspect of the invention is an immunopotentiating composition comprising an immunopotentiating amount of substantially pigment-free GBA admixed with a pharmaceutically acceptable vehicle.

BRIEF DESCRIPTION OF THE DRAWINGS

FIG. 4 is a graph of the results of the in vivo adjuvanticity tests described in the example.

MODES OF CARRYING OUT THE INVENTION

Figure 1:
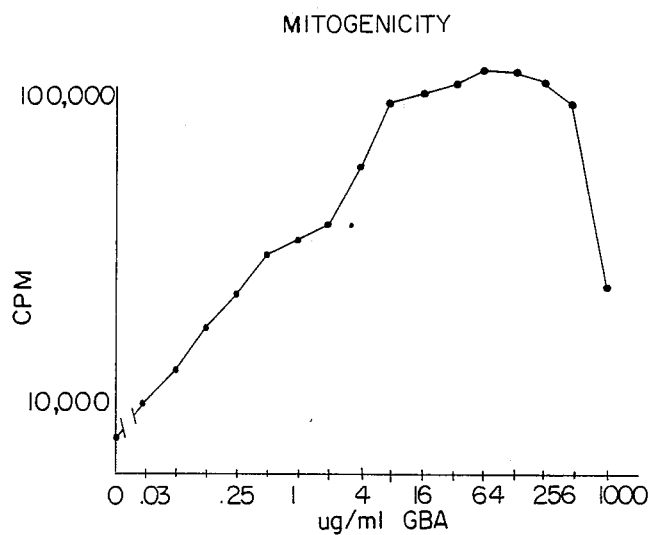
FIG. 1 is a graph of the results of the mitogenicity tests described in the example.

Cytophaga strain GB-2 was deposited at the American Type Culture Collection (ATCC) 12301 Parklawn Drive, Rockville, Md., U.S.A. on 25 Apr. 1986 under accession number 53485 pursuant to the provisions of the Budapest Treaty. This deposit will be maintained and made accessible to others in accordance with the provisions of that Treaty. Availability of the deposited strain is not to be construed as a license to practice the invention in contravention of the rights granted under the authority of any government in accordance with its patent laws.

The deposit of the strain does not constitute an admission that the written description of this application is inadequate to enable the practice of the any aspect of the invention, including the best mode thereof, nor is it to be construed as limiting the scope of the claims.

GB-2 grows only at temperatures below 30° C. and is killed at 37° C., with an optimal growth temperature of 25° C.–28° C. when cultured in mineral salts, 0.5% glucose, 1% lactalbumin hydrolysate media or in media E (*J Biol Chem* (1956) 218:97–106) supplemented with at least 0.1% glucose. Aeration of GB-2 is essential since cultures in log growth cease to divide once shaking is stopped. The bacteria are able to utilize glucose galactose, cellobiose, xylose, arabinose, saccharose, starch casein, or gelatin but not potassium-acetate, sodium lactate, glycerol chitin, or cellulose as substrates when inoculated onto minimal media agar plates consisting of mineral salts, yeast extract, and agar and cultured under aerobic conditions. No anaerobic growth of GB-2 was observed under these conditions; however the bacteria grew anaerobically on TS-blood agar plates in an atmosphere of nitrogen. GB-2 grows better when cultured in the presence of filter-sterilized glucose than autoclaved glucose. Cultures supplemented with autoclaved glucose grow more slowly, less densely and tolerate a narrower range of glucose concentrations as compared to cultures grown in filtered glucose.

GB-2 is a gram-negative rod, that does not produce flagella but is capable of gliding mobility on agar supplemented with the media described above. Gliding was not observed when the bacteria were grown on standard Merck agar plates. Light and electron microscopy failed to show the production of fruiting bodies or microcysts by GB-2. By these criteria GB-2 is a member of the order Cytophagales.

GB-2, whether grown in aerobic an anaerobic conditions, synthesizes a yellow pigment which by spectral absorption analysis is believed to be flexirubin. The production of yellow pigment is characteristic of bacteria in the family Cytophagaceae within the order Cytophagales. The presence of the yellow pigment flexirubin is a useful chemosystematic marker for bacteria in the Cytophaga/Flexibacteria group. This noncarotenoid, upon treatment with 20% KOH, undergoes a spectral shift from yellow to red-violet. GB-2, as well as the yellow pigmented substances produced by GB-2, undergo a similar change in color upon this alkaline treatment.

Other characteristics displayed by GB-2 support its classification into the Cytophaga/Flexibacteria group. GB-2 was able to grow anaerobically and produced as major fermentation products succinic, acetic, lactic, propionic, and butyric acids. Most species of Cytophaga and Flexibacteria are aerobic bacteria but some species are facultative producing succinic acetic, lactic, propionic, and butyric acids as the major fermentation products. Furthermore, GB-2 possessed both catalase and oxidase enzyme activities, as do bacteria of these genera. The inability to distinguish clearly between Cytophaga and Flexibacteria genera stems largely from the lack of data on the unique characteristics of these bacteria. Although there are several exceptions, most species of Cytophaga are able to utilize complex carbohydrates like starch as a source of carbon, while species of Flexibacteria are generally able to utilize only simple sugars. GB-2 grows well on starch and therefore is consistent with its tentative classification as a member of Cytophaga.

Substantially pigment-free GBA is isolated from medium in which Cytophaga GB-2 has been cultured in the following manner. The bacteria are first separated from the medium by centrifugation. Preferably the supernatant is then concentrated fifty to one-hundred fold by ultrafiltration. The major contaminants in the concentrated supernatant are yellow pigment (presumably flexirubin), protein and LPS.

The next step in the isolation is the removal of pigment from the GBA by repeated extraction with acetone. Acetone is first mixed with the concentrated supernatant under conditions that cause the GBA to precipitate, leaving the pigment in solution. The precipitation is carried out at reduced temperatures. preferably $-40°$ C. to $-10°$ C., and most preferably approximately $-20°$ C. using an acetone:supernatant volume ratio in the range of about 8:1 to about 4:1, preferably about 5:1. The maximum light absorption by the pigment occurs at 455 nm and its presence in the precipitate may be monitored spectrophotometrically. In order to reduce the amount of pigment in the precipitate to undetectable levels as measured by absorbance at 455 nm, the precipitate is repeatedly dissolved in an aqueous medium and reprecipitated with acetone under the conditions given above.

After the pigment has been extracted protein and nucleic acid contamination may be lowered by enzymatic digestion followed by gel filtration of the digest in the presence of detergent, preferably a nonionic detergent such as Np-40 or a Triton detergent. Depending upon the conditions for enzymatic activity the digestion may have to be carried out in a plurality of steps. The precipitate is first dissolved and optionally dialyzed with water and the pH of the solution is adjusted to that at which the enzyme is active. If necessary, factors necessay for enzymatic activity are added to the solution. Since the purpose of the digestion is to degrade proteins and nucleic acids nonspecifically, it is preferable to use nonspecific nucleases and proteases such as DNase, RNase, pronase and pepsin in the digestion. Following the digestion, gel filtration is used to remove the low molecular weight protein and nucleic acid fragments from the higher molecular weight GBA. Nonionic detergent is added to the digest to promote complexing of the contaminants into micelles that are more easily removed by sizing. Gels in which GBA runs in the void while the contaminants are retarded is used. Preferably the gel has an exclusion point greater than about 200,000 daltons.

LPS may he removed from the purified GBA by affinity chromatography using a ligand that binds LPS, such as a polymyxin-B agarose column. LPS in the purified GBA will be retained by the column.

The resulting substantially pure GBA contains no pigment as determined by absorbance at 455 nm, less than about 0.5% by weight protein as measured by the amino acid analysis method, and less than about 0.01% by weight LPS as measured by the Limulus gelation assay. Electron micrographs of this purified GBA shows that it exists as spherical particles about 200 to 1200 A° in diameter. Its molecular weight is estimated by gel permeation chromatography and electron microscopy at about $10^6$ to $10^8$ daltons. The extreme water solubility of GBA and its reactivity in the phenol-sulfuric hexose assay suggest it is a polysaccharide. Elemental analysis of purified GBA is consistent with GBA being a polysaccharide. GBA (as measured by biological activity) is stable to treatment with strong base (1.5 M sodium hydroxide), chaotropic agents (potassium thiocyanate and guanidine hydrochloride), and detergent (NP-40).

EXAMPLES

The following disclosure further illustrates the production and characterization of GBA and its biological activities. The following disclosure is not intended to limit the invention in any manner.

Production of GBA Exopolymer

Two hundred liters of a Cytophaga species GB-2 was grown to late log phase in defined, dialyzable medium E. Bacteria were removed by continuous centrifugation and supernatant was concentrated 50–100 fold by ultrafiltration (Pelican, Millipore Inc. Bedford, Mass.). The filtrate was recentrifuged (10,000×g for 45 min). The supernatant was frozen until further use.

Aliquots of crude exopolymer were precipitated with $-20°$ C. acetone at a 5:1 v/v ratio (acetone:supernatant) and allowed to stand at 4° C. for at least 2 hr prior to centrifugation (2,000×g for 15 min). Precipitates were redissolved with water and reprecipitated, as above, four more times. The final precipitate was dissolved and dialyzed against water and was digested at 37° C. with mixing overnight with DNase and RNase (neutral pH. 5 mM $Mg^{++}$, 100 μg of each enzyme/ml). The pH was adjusted to 4 with acetic acid and pepsin (200 μg/ml) was added. After overnight mixing at 37° C., NP-40 was added (0.1% final concentration) and the mixture was neutralized and boiled for 10 min. Aliquots were then passed over a column of Sephacryl-300 gel. Material in the void volume of the gel was collected and dialyzed exhaustively against water and passed over a 10 ml column of polymyxin-B agarose and lyophilized.

Various physical and chemical analyses of the crude and purified GBA exopolymer were carried out. Table 1 below summarizes the results of those analyses.

TABLE 1

| Physical and Chemical Properties of GBA | | |
|---|---|---|
| | Crude | Pure |
| Protein (Bradford) (BSA as standard) | 3-11% | <0.5% |
| Nucleic acid | Substantial $A_{260}$* | $A_{260}{}^{1\%} = 0$* |
| Endotoxin (Limulus) | 0.5-1% | 0.01-0.05% |
| Pigment | $A_{455}{}^{1\%} > 3.0$ | $A_{455}{}^{1\%} < 0.05$ |
| Size | 3 disparate size classes: $10^7, 10^5, 10^3 M_r$ | runs in void volume of S-1000 sizing column ($M_r = 10^6$) |
| Electron microscopy | Interconnected globular particles | Spherical particles: $2 \times 10^6 - 4 \times 10^7$ daltons |
| Sedimentation | Biologically active particles pellet at 100,000 × g in 1 hr | Same |
| Elemental analysis | Not tested | C 47.08; H 7.11; N 5.83 O 39.99 |
| 1° Amines (fluorescamine) | Not tested | <0.02% |
| Charge | Not tested | Positively charged at pH 8.6 and migrates in a single band as determined by IEP |

Based on the chemical analysis of the exopolymer, it is believed to be an amino sugar polymer with no primary amines or cis-hydroxyls.

The following studies were carried out to evaluate various aspects of the biological activity of purified GBA.

B Cell Mitogenicity

Murine spleen cells were cultured in medium containing various quantities of purified GBA. After 48 hr the cultures were pulsed with tritiated thymidine. The cells were harvested 18 hr after the pulse and tritiated thymidine incorporation was measured with a scintillation counter. FIG. 1 is a graph of the results with incorporation expressed as counts per minute (cpm) plotted against GBA concentration.

Polyclonal Activation

Figure 2:
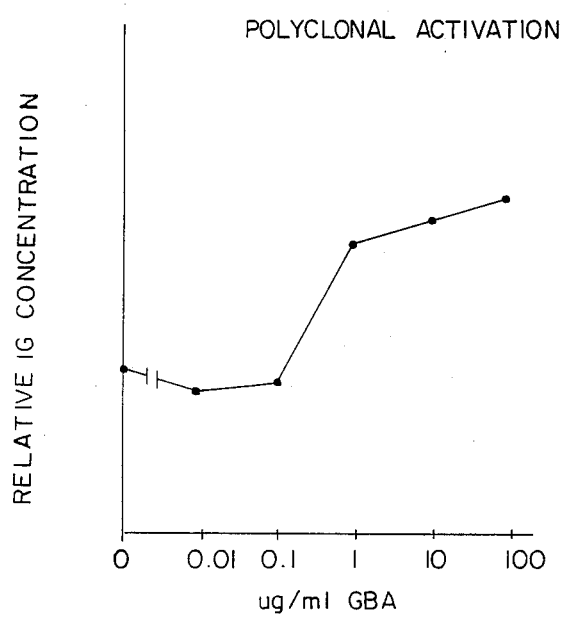
FIG. 2 is a graph of the results of the polyclonal activation tests described in the example.

Murine spleen cells were cultured in medium containing various concentrations of GBA for four days. Supernatants were then assayed for murine Ig using a standard enzyme-linked immunosorbent assay (ELISA). FIG. 2 is a graph of the assay with relative Ig concentration plotted against GBA concentration.

In Vitro Adjuvanticity

Figure 3:
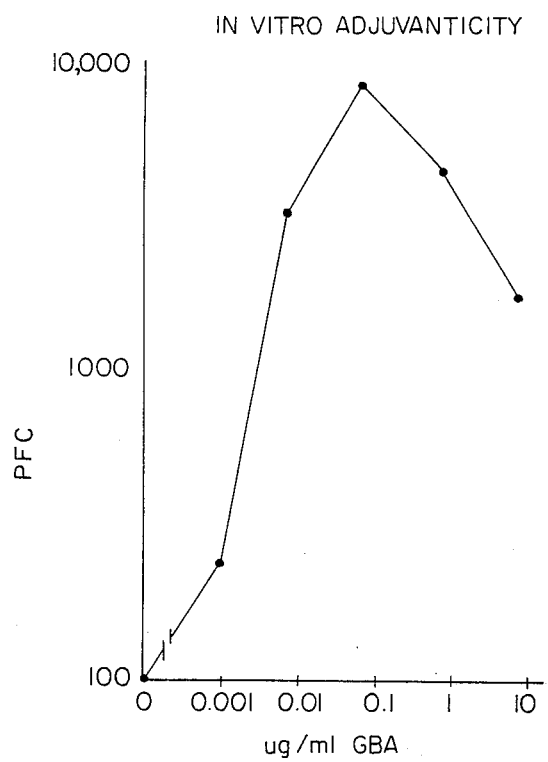
FIG. 3 is a graph of the results of the in vitro adjuvanticity tests described in the example.

Adjuvanticity of GBA was evaluated by the Mishell-Dutton culture assay. In this assay mouse spleen cells were cultured with sheep red blood cells for five days in 1 ml of medium supplemented with 5% FCS (selected lots) and various amounts of purified GBA. FIG. 3 is a plot of the results of this test.

In Vivo Adjuvanticity

Two pairs of Balb/c mice were injected i.p. with 10 μg of cytochrome C (a suboptimal amount of antigen) with and without 50 μg purified GBA emulsified in PBS containing 0.2% Tween® 80 surfactant, 2.5% Pluronic® L121 surfactant, and 5% squalane. Serum antibody titers were determined 9-11 days post injection by enzyme immunoassay. FIG. 4 is a plot of the assay results.

Induction of IL-1 Production by Macrophages

Figure 5:
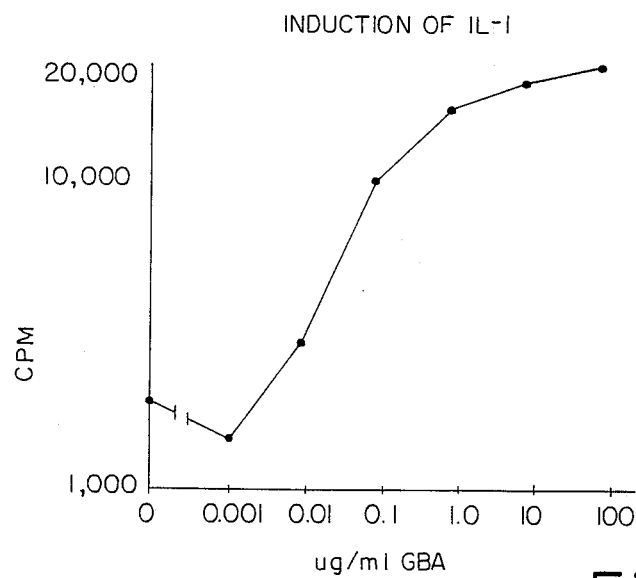
FIG. 5 is a graph of the results of the IL-1 induction tests described in the example.

Murine macrophage cells (WEHI 265) were cultured for three days in media containing various amounts of purified GBA. Culture supernatants were tested for IL-1 content by the thymocyte comitogen assay (measuring incorporation of tritiated thymidine by cultured murine thymocytes). FIG. 5 is a graph of the results with tritiated thymidine incorporation expressed as cpm plotted against GBA content.

As shown in FIGS. 1-5, GBA was effective in potentiating the investigated activities at the nanogram level except for polyclonal activation. Comparison of specific activities for the purified GBA observed in the B cell mitogenicity assay and the IL-1 induction assay with specific activities observed for crude GBA in these assays show that the pure material is approximately 50-100 fold more active than the crude material. Such an increase is much greater than would be expected simply due to removal of inactive substances. In this regard it is believed that the difference in activity is due to inhibition of activity by one or more of the removed substances, most likely the pigment.

Other in vitro tests have shown that GBA induces human peripheral blood monocytes to secrete IL-1.

Induction of Natural Killer (NK) Cell Activity

Two strains of mice, C57B1/6J and C57B1/CR1, were injected i.p. with either saline, 100 μg poly (IC), or 50 μg GBA. Spleens were removed 18 hr after injection and assayed for cytotoxic activity against $^{51}Cr$-labeled YAC target cells. Table 2 presents the results of the assays.

TABLE 2

| Effector Target Ratio | Strain I (C57B1/CRL) | | | Strain II (C57B1/6) | | |
|---|---|---|---|---|---|---|
| | None | GBA* | Poly (IC) | None | GBA* | Poly (IC) |
| 25 | 0.9 | 3.4 | 12.1 | ** | 6.9 | 12.5 |
| 50 | 8.5 | 15.9 | 25.2 | ** | 12.7 | 22.0 |
| 100 | 9.6 | 24.5 | 33.9 | ** | 11.8 | 32.3 |

*Number in these columns are averages of specific NK activity from two mice.
**Although not performed in this assay, spontaneous NK activity (no inducer) invariably averages 10% or less for this strain and age of mice.

As indicated, GBA induced significant activity in one of the strains of mice.

GBA is nonspecies specific in its biological activity and is, therefore, useful in potentiating immune responses in vertebrate subjects in general, including humans. It will typically be used in prophylactic or therapeutic treatment of humans, domestic animals such as cattle, horses sheep and pigs, or sports and pet animals such as cats and dogs. In a prophylactic setting the pigment-free GBA will typically be incorporated into animal or human vaccines, particularly those considered "weak" vaccines (i.e., those that provide diminished protection in terms of level, extent, and/or duration). Examples of such vaccines are bacterins such as Bordetella bacterin, *Escherichia coli* bacterins, Haemophilus bacterins, Leptospirosis bacterins, *Moraxella bovis* bacterin, Pasteurella bacterin and *Vibrio fetus* bacterin; and attenuated live or killed virus products such as bovine respiratory disease vaccine (infectious bovine rhinotracheitis, parainfluenze-3, respiratory syncytial virus), bovine virus diarrhea vaccine, equine influenza vaccine, feline leukemia vaccine, feline respiratory disease vaccine (rhinotracheitis calici-pneumonitis viruses), canine parvovirus vaccine. transmissible gastroenteritis vaccine, Newcastle disease virus vaccine, and pseudorabies vaccine. The adjuvant may also be used with various recombinant or subunit vaccines.

Accordingly, the vaccines will contain an immunogen that is effective in immunizing a patient against a given pathogen or antigen a pharmaceutically acceptable vaccine carrier, and an immunopotentiating amount of pigment-free GBA. If desired, the vaccine formulation may contain minor amounts of other conventional vaccine additives such as surfactants and preservatives. The particular formulation will depend upon the individual being immunized, the immunogen, and the vaccination regimen. A preferred vaccine vehicle for use in formulating the immunogen and GBA is phosphate-buffered saline (PBS) containing a Pluronic® nonionic surfactant such as Pluronic® L121 surfactant (Pluronic® surfactants are polyoxyalkylene derivatives of propylene glycol), a Tween® surfactant, such as Tween® 80 surfactant (Tween® surfactants are polyoxyethylene derivatives of fatty acid partial esters of sorbitol anhydrides), and squalane. This formulation may be prepared by: mixing the surfactants and squalane in PBS: adding the adjuvant to the mixture with agitation to form a vehicle-adjuvant mix having the consistency of thin milk; and then adding the immunogen in PBS to the adjuvant-vehicle mix. Preferred concentrations of the vehicle additives are Tween® surfactant, 0.2%, Pluronic® surfactant 2.5%, and squalane, 5%. Alternatively, again depending upon the individual, immunogen and regimen it maY be desirable to coadminister the GBA as a separate formulation. As yet another alternative it may be desirable to covalently bond the immunogen to the GBA by conventional methods used to couple or conjugate antigens to carriers.

The GBA of the invention may also be used as a prophylactic for potentiating a nonspecific response. Such treatment is used for instance, to protect animals or humans from conditions such as shipping fever in the case of domestic animals, or immunosuppression due to disease, chemotherapy or other causes. Further, the GBA may be used in a therapeutic setting to treat immunodeficiencies such as congenital deficiencies or deficiencies caused bY viral or other infections.

The GBA will normally be administered in amounts ranging between about 1 μg to 1 mg. The particular amount will depend upon the individual being treated, that individual's history the mode of administration, the formulation, and the condition for which the GBA is being administered. The GBA will normally be administered parenterally (e.g., by injection). Oral administration, however may be feasible. Depending upon the purpose of the administration, administration via a sustained release formulation, such as via an implant, may be desirable.

Modifications of the above described modes of carrying out the invention that are obvious to those of skill in the fields of microbiology, biochemistry. immunology and/or pharmacology are intended to be within the scope of the following claims.

We claim:

1. Substantially pigment-free gliding bacteria adjuvant (GBA) of Cytophaga species GB-2 (ATCC Accession No. 53485), the GBA being an exopolymer polysaccharide having a spectral absorption at 455 nm of less than about 0.05 in a 1% aqueous solution and containing less than about 0.5% by weight protein and less than about 0.1% by weight lipopolysaccharide.

2. A method of isolating the adjuvant of claim 1 from a medium in which Cytophaga GB-2 has been cultured comprising precipitating GBA from the medium with acetone, repeatedly redissolving the GBA in an aqueous medium and reprecipitating the GBA with acetone until the spectral absorption at 455 nm of a 1% aqueous solution of the precipitate is less than 0.05 and thereafter removing protein therefrom to a level of less than about 0.5% by weight and lipopolysaccharide therefrom to a level of less than about 0.1% by weight.

3. The method of claim 2 wherein residual protein and nucleic acids are removed from the precipitated GBA by enzymatic digestion and filtration and residual lipopolysaccharide is removed from the precipitated GBA by affinity chromatography.

4. The method of claim 3 wherein the nucleic acids and proteins are digested with nonspecific enzymes, a detergent is added to the digest to facilitate micelle complexing of the digested substances, filtration is effected with a gel that passes the GBA and retards micelle complexes of the digested substances, and the affinity chromatography is effected with a polymyxin-B agarose column.

5. A method of potentiating an immune response in a subject comprising administering an immunopotentiating amount of the adjuvant of claim 1 to the subject.

6. A method of enhancing the immune response of an individual to a vaccine comprising coadministering an immunopotentiating amount of the adjuvant of claim 1 as part of the vaccination regimen.

7. An immunopotentiating composition comprising the adjuvant of claim 1 combined with a pharmaceutically acceptable vehicle.

8. A vaccine composition comprising an effective amount of an immunogen and an immunopotentiating amount of the adjuvant of claim 1 combined with a pharmaceutically acceptable vehicle.

* * * * *